United States Patent [19]

Cleary et al.

[11] Patent Number: 6,120,289
[45] Date of Patent: Sep. 19, 2000

[54] ORTHODONTIC ATTACHMENT DEVICE FOR INTERARCH APPLIANCES

[75] Inventors: James D. Cleary, Glendora; William E. Wyllie, II, Sierra Madre; Brian W. Lotte, Hermosa Beach, all of Calif.

[73] Assignee: 3M Innovative Properties Company, St. Paul, Minn.

[21] Appl. No.: 09/275,490

[22] Filed: Mar. 24, 1999

[51] Int. Cl.$^7$ .................................................. A61C 3/00
[52] U.S. Cl. .............................................. 433/22; 433/19
[58] Field of Search ................... 433/22, 18, 19, 433/21, 2

[56] References Cited

U.S. PATENT DOCUMENTS

| | | | |
|---|---|---|---|
| 3,508,332 | 4/1970 | Armstrong | 433/21 |
| 3,798,773 | 3/1974 | Northcutt | 32/14 |
| 3,997,970 | 12/1976 | Hodgson | 433/19 |
| 4,462,800 | 7/1984 | Jones | 433/19 |
| 4,551,095 | 11/1985 | Mason | 433/19 |
| 4,618,324 | 10/1986 | Nord | 433/19 |
| 4,708,646 | 11/1987 | Jasper | 433/19 |
| 4,795,342 | 1/1989 | Jones | 433/19 |
| 5,352,116 | 10/1994 | West | 433/19 |
| 5,435,721 | 7/1995 | Vogt | 433/19 |
| 5,562,445 | 10/1996 | DeVincenzo et al. | 433/19 |
| 5,651,672 | 7/1997 | Cleary et al. | 433/19 |
| 5,711,667 | 1/1998 | Vogt | 433/19 |
| 5,718,576 | 2/1998 | Schnaitter et al. | 433/22 |

FOREIGN PATENT DOCUMENTS

| | | |
|---|---|---|
| 195 26 474 | 1/1997 | Germany . |

OTHER PUBLICATIONS

Jasper Jumper Color Atlas, by Franz–Peter Schwindling, pp. 31–39, 78–81, 85–89, 1997.

Jasper Jumper manual, American Orthodontics, date unknown.

*Primary Examiner*—John J. Wilson
*Assistant Examiner*—Melba Bumgarner
*Attorney, Agent, or Firm*—James D. Christoff

[57] ABSTRACT

An attachment device useful during the course of orthodontic treatment couples an interarch appliance to brackets and/or to archwires placed in the oral cavity. The attachment device includes a wire segment that crosses over a labial side of an archwire in order to enable a coupler of the interarch appliance to slide past the archwire as the patient's jaws are opened. The attachment device increases the range of free sliding motion of the interarch appliance and reduces the amount of stress that might be otherwise imposed on the appliance, on the brackets and/or the archwires as the patient's jaws are opened. The attachment device is particularly suitable for use with Class II correction appliances including elongated, resilient force modules that have an inherent bias toward a normally straight orientation.

32 Claims, 7 Drawing Sheets

ORTHODONTIC ATTACHMENT DEVICE FOR INTERARCH APPLIANCES

BACKGROUND OF THE INVENTION

1. Field of the Invention

This invention relates to a coupling or attachment device that is useful in orthodontic treatment. More particularly, the present invention concerns an attachment device for connecting an interarch appliance such as a Class II correction appliance to appliances secured to the patient's dental arches.

2. Description of the Related Art

Orthodontic treatment involves movement of malpositioned teeth to orthodontically correct positions. During treatment, tiny orthodontic appliances known as brackets are often connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to the patient's molar teeth. The system of brackets, archwires and buccal tubes are commonly referred to as "braces".

The orthodontic treatment of some patients include correction of the alignment of the upper dental arch with the lower dental arch. For example, certain patients have a condition referred to as a Class II malocclusion where the lower dental arch is located an excessive distance in a rearwardly direction relative to the location of the upper dental arch when the jaws are closed. Other patients may have an opposite condition referred to as a Class III malocclusion wherein the lower dental arch is located in a forwardly direction of its desired location relative to the position of the upper dental arch when the jaws are closed.

Orthodontic treatment of Class II and Class III malocclusions are commonly corrected by movement of the upper dental arch as a single unit relative to movement of the lower dental arch as a single unit. To this end, forces are often applied to each dental arch as a unit by applying force to the brackets or buccal tubes, the archwires, or attachments connected to the brackets, buccal tubes, or archwires. In this manner, a Class II or Class III malocclusion can be corrected at the same time that the archwires and the brackets are used to move individual teeth to desired positions relative to each other.

Correction of Class II and Class III malocclusions is sometimes carried out by use of a force-applying system known as headgear that includes strapping which extends around the rear of the patient's head. The strapping is often connected by tension springs that, in turn, are connected to the buccal tubes, the brackets or one of the archwires. Additionally, as an alternative for correction of Class III malocclusions, the strapping may be connected by tension springs to a chin cup that externally engages the patient's chin. In either instance, the strapping and springs serve to apply a rearwardly-directed force to the associated jaw.

However, headgear is often considered unsatisfactory because it is visibly apparent. Headgear may serve as a source of embarrassment, particularly among adolescent patients who may experience teasing from classmates. The embarrassment can be somewhat reduced if the orthodontist instructs the patient to wear the headgear only at night, but unfortunately such practice may lengthen treatment time since the desired corrective forces are applied during only a portion of each calendar day.

Consequently, many practitioners and patients favor the use of intra-oral devices for correcting Class II and Class III malocclusions. Such devices are often located near the cuspid, bicuspid and molar teeth and away from the patient's anterior teeth. As a result, intra-oral devices for correcting Class II and Class III malocclusions are hidden in substantial part once installed and eliminate much of the patient embarrassment that is often associated with headgear.

Orthodontic force modules made of an elastomeric material have been used in the past to treat Class II and Class III malocclusions by connecting a pair of such force modules between the dental arches on opposite sides of the oral cavity. Elastomeric force modules are often used in tension to pull the jaws together in a direction along reference lines that extend between the points of attachment of each force module. Such force modules may be an O-ring or a chain-type module made of a number of integrally connected O-rings. However, these modules are typically removable by the patient for replacement when necessary, since the module may break or the elastomeric material may degrade during use to such an extent that the amount of tension exerted is not sufficient.

Unfortunately, orthodontic devices such as headgear and removable force modules are not entirely satisfactory for use with some patients, because the effectiveness of the devices is dependent upon the patient's cooperation. Neglect of the patient to faithfully wear the headgear each day or install new elastomeric force modules as appropriate can seriously retard the progress of treatment and defeat timely achievement of the goals of an otherwise well-planned treatment program, resulting in an additional expenditure of time for both the patient and the orthodontist.

As a consequence, a number of intra-oral devices that are non-removable by the patient have been proposed in the past to overcome the problems of patient cooperation associated with headgear and with removable intra-oral force modules. For example, U.S. Pat. Nos. 4,708,646, 5,352,116, 5,435,721 and 5,651,672 describe intra-oral devices with flexible members that are connected to upper and lower dental arches of a patient. The length of the members is selected such that the member is curved in an arc when the patient's jaws are closed. The members have an inherent bias that tends to urge the members toward a normally straight orientation to provide a force that pushes one dental arch forwardly or rearwardly relative to the other dental arch when the jaws are closed.

Other orthodontic devices for correcting Class II and Class III malocclusions are described in U.S. Pat. Nos. 3,798,773, 4,462,800 and 4,551,095. The devices described in these references include telescoping tube assemblies that urge the dental arches toward positions of improved alignment. The assemblies are securely coupled to other orthodontic appliances such as brackets or buccal tubes by the practitioner, and the problems of patient non-compliance are avoided.

Another type of telescoping tube assembly for repositioning the dental arches is described in U.S. Pat. No. 5,711,667. In this patent, a spring is provided to urge a plunger in a direction away from a cylinder to achieve desired movements of the patient's teeth. The spring is described in this reference as being located within the cylinder or external of the cylinder in either coaxial relation or offset, parallel relation to the central axis of the plunger.

U.S. Pat. No. 5,562,445 describes another intra-oral device for moving the position of one dental arch relative to the other. The device disclosed in U.S. Pat. No. 5,562,445 includes first and second telescoping cylinders and a plunger received in the first cylinder. A spring in the first cylinder urges the plunger and the first cylinder in directions away from each other, while the first cylinder and the second cylinder are freely slidable relative to each other.

In the past, it has been common practice to connect the lower end of many of the non-removable intra-oral devices mentioned above to the archwire on the lower dental arch in a space between a pair of adjacent brackets. For example, the devices described in U.S. Pat. Nos. 4,708,646, 5,352,116, 5,435,721 and 5,651,672 have an opening near the lower end of the appliance that is used to receive the mandibular archwire. Similarly, the upper end of the appliance also has an opening that may be used to receive a pin having an enlarged head and a stem that is received in a passage of a buccal tube or other appliance fixed to one of the patient's upper molar teeth.

Preferably, the lower end of the appliances described in U.S. Pat. Nos. 4,708,646, 5,352,116, 5,435,721 and 5,651,672 slides freely in a distal direction along adjacent portions of the mandibular archwire as the patient's jaws are opened and closed. If, for example, such sliding movement is hindered, repeated opening and closing of the patient's jaws may fatigue the appliances, the associated pins or the mandibular archwire to such a degree that breakage may occur. In many instances, the orthodontist will remove brackets affixed to the patient's bicuspid teeth in order to increase the distance that the lower end of the appliances can slide along adjacent portions of the lower archwire.

Unfortunately, removal of the bicuspid brackets to increase the range of sliding movement of the correction devices mentioned above can retard treatment in some instances. For example, movement of the bicuspid teeth toward final desired positions for orthodontically correct occlusion is hindered during the time that the bicuspid brackets are not in place. The bicuspid brackets can be rebonded to the bicuspid teeth in order to help move the latter once the Class II correction appliances are removed, but such a procedure is somewhat time consuming and may extend the overall length of treatment time.

Occasionally, orthodontists have attempted to avoid the problems noted above by connecting the lower end portion of Class II correction appliances to an auxiliary wire that extends along the lower archwire. In some instances, the auxiliary wires are soldered by the orthodontist on both ends to the lower archwire, and a ball stop is provided to engage the mesial side of the lower end portion of the appliance. However, such a practice is often considered unsatisfactory because the auxiliary wire must be soldered in place before the archwire is placed in the brackets, resulting in additional work for the orthodontist. Furthermore, the soldered joint may break apart in use and interrupt the progress of treatment, and also necessitate a return visit by the patient to the orthodontist.

In other past instances, an auxiliary wire has been fashioned by the orthodontist with a hook on one end for coupling to an archwire. The other end of such wires has either a hook for coupling to the archwire or a straight section for insertion into a buccal tube. However, it is somewhat time consuming for the orthodontist to cut and shape such an auxiliary wire, and the results are often not entirely satisfactory.

An improved attachment device for intra-oral orthodontic appliances is described in U.S. Pat. No. 5,718,576 and includes an elongated wire that extends for a majority of its length along the archwire in side-by-side relation. That device also includes a crimpable connector fixed to the wire and having wall portions that are deformable in directions toward a passageway of the connector for non-rotatable connection to the archwire.

The attachment device described in U.S. Pat. No. 5,718,576 is advantageous because it enables the lower end of an interarch appliance such as a Class II correction appliance to travel freely a significant distance whenever the patient's jaws are opened without imposing undue stress on the appliance, on the lower archwire or on adjacent brackets. Moreover, none of the brackets normally need be removed for installation or use of the device or appliance. The crimpable connector securely fixes the device to the archwire in an easy manner without the need for soldering and also prevents the attachment device from rotating about the longitudinal axis of the lower archwire, which otherwise might cause the appliance to catch or bind against another appliance in the oral cavity.

While the device described in U.S. Pat. No. 5,718,576 represents a significant advance in the art, there is a continuing need to improve the performance of orthodontic devices and appliances in order to enhance treatment results and increase patient satisfaction. For example, it is important for orthodontic appliances and devices to function in a reliable manner for extended periods of time between appointments. If one of the appliances or devices fails during the course of treatment, the progress of treatment is often interrupted until such time as the patient returns to the orthodontist for repair or replacement of the malfunctioning part. As can be appreciated, such a malfunction represents a time-consuming nuisance for both the practitioner and the patient, and may result in additional expense.

Moreover, it would be desirable to increase patient comfort during the course of orthodontic treatment. Orthodontic appliances are widely regarded as uncomfortable and any reduction in the level of patient discomfort that is achieved would be considered an improvement over existing appliances.

SUMMARY OF THE INVENTION

The present invention concerns an improved orthodontic attachment device especially useful for interarch appliances such as Class II correction appliances. The attachment device includes a wire segment that is oriented to enable the interarch appliance to freely move a greater distance than possible with previous attachment devices as the patient's jaws are opened. The additional range of movement provided by the attachment device of the present invention reduces the likelihood that undue amounts of stress will be imposed on brackets, buccal tubes, archwires or other orthodontic elements in the oral cavity. As a result, the likelihood of breakage or other malfunctions of the various elements during the course of treatment is substantially reduced. Moreover, such construction decreases the amount of resistance presented by the various orthodontic elements to opening movement of the patient's jaws and provides greater comfort to the patient as a result.

In more detail, the present invention in one aspect concerns an orthodontic assembly comprising an orthodontic system that includes a set of brackets and an archwire connected to each bracket. The assembly additionally includes an interarch appliance for repositioning the lower dental arch relative to the upper dental arch, and the interarch appliance includes a coupler. The assembly also includes an attachment device connected to the system, and the attachment device includes a wire segment. The coupler of the interarch appliance is connected to the wire segment for sliding movement along the length of the wire segment. The wire segment crosses over the labial side of the archwire with sufficient space between the wire segment and the archwire such that the coupler of the interarch appliance is movable past the archwire as the patient's jaws are opened.

Another aspect of the present invention also relates to an orthodontic assembly. In this aspect, the assembly comprises a maxillary orthodontic system that includes a set of maxillary brackets and a maxillary archwire connected to each maxillary bracket. The assembly additionally includes a mandibular orthodontic system that includes a set of mandibular brackets and a mandibular archwire connected to each mandibular bracket. The assembly also includes an interarch appliance for repositioning the mandibular dental arch relative to the maxillary dental arch. The interarch appliance includes an upper end portion connected to the maxillary system, and the interarch appliance also includes a lower end portion having a coupler. The assembly further includes an attachment device connected to the mandibular system, and the attachment device includes a wire segment. The coupler of the interarch appliance is connected to the wire segment for sliding movement along the length of the wire segment. The wire segment crosses over the labial side of the mandibular archwire with sufficient space between the wire segment and the mandibular archwire such that the coupler of the interarch appliance is movable past the mandibular archwire as the patient's jaws are opened.

The present invention is also directed to an orthodontic coupling pin. The pin comprises a shank and linkage connected to the shank. The linkage is articulated.

Other aspects and advantages of the invention are set out in the detailed description that follows and are illustrated in the accompanying drawings.

DETAILED DESCRIPTION OF THE PREFERRED EMBODIMENTS

Figure 1:
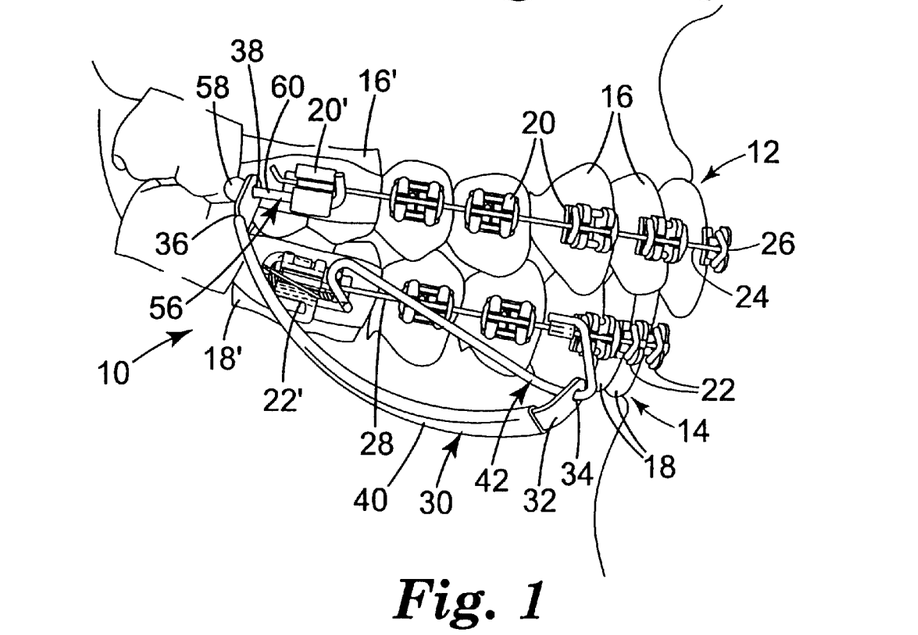
FIG. 1 is a side elevational view of an orthodontic assembly constructed according to one embodiment of the present invention, wherein the assembly is shown for exemplary purposes as connected to upper and lower dental arches of a patient undergoing orthodontic treatment.

An orthodontic assembly according to one embodiment of the invention is illustrated in FIG. 1 and is broadly designated by the numeral 10. The assembly 10 is used in the oral cavity, and in particular is attached to the patient's upper or maxillary dental arch 12 as well as to the lower or mandibular dental arch 14. The upper dental arch 12 includes a set of upper or maxillary teeth 16, and the lower dental arch 14 includes a set of lower or mandibular teeth 18.

A set of maxillary orthodontic brackets 20 is mounted on the patient's upper teeth 16, and includes a maxillary buccal tube bracket 20' that is fixed to a band mounted on one of the patient's upper molar teeth 16', such as a first molar tooth as shown in the drawings. The brackets 20 depicted in FIG. 1 as well as in the remaining drawings represent examples of suitable brackets, and in this instance the brackets 20 are twin tiewing brackets. However, various alternative brackets of other configurations such as single tiewing brackets, self-ligating brackets or other brackets may also be employed. The brackets may be made of metal, ceramic, plastic or any other suitable material known in the art.

The assembly 10 also includes a set of mandibular brackets 22 that are connected to the patient's lower teeth 18. The brackets 22 may be similar to or different from the brackets 20 described above. The brackets 22 include two buccal tube brackets 22' (only one is shown) that are each fixed to a band mounted on a lower respective molar tooth 18'.

As shown in FIG. 1, the buccal tube brackets 20', 22' are mounted for purposes of illustration on bands, and are preferably welded to bands that encircle the patient's molar teeth 16', 18' respectively. However, as another option, the buccal tubes 20', 22' may be directly bonded to the outer surfaces of the patient's molar teeth 16', 18' if desired. The use of bands for buccal tube brackets is preferred by many practitioners, because the bands provide a secure mounting location for the buccal tube brackets and substantially reduce the likelihood of spontaneous, unintentional detachment of the buccal tube brackets from the associated teeth. The bands are omitted in the remaining views.

Each of the brackets 20 has an archwire slot that extends in a generally mesial-distal direction. A maxillary archwire 24 is placed in the slot of each maxillary bracket 20 as well as into a passage of the maxillary buccal tube bracket 20'. The archwire 24 is held in place in each of the brackets 20 by a ligature 26, which in this instance is a small elastomeric ligature having the shape of a O-ring. Alternatively, wire ligatures having ends that are twisted together may also be used to ligate the archwire 24 to the brackets 20. The brackets 20, 20' and the archwire 24 comprise a maxillary orthodontic system.

Similarly, each of the mandibular brackets 22 has an archwire slot, and a mandibular archwire 28 is placed in the slot of each bracket 22. Ends of the archwire 28 extend through passages of the buccal tube brackets 22' (only one is shown in the drawings). The archwire 28 is ligated to the brackets 22 by means of ligatures (shown in FIG. 1 but omitted in FIG. 2) similar to ligatures 26. Distal ends of each archwire 24, 28 are bent as shown in FIG. 1 to help retain the archwires 24, 28 in the passages in the respective buccal tube brackets 20', 22' respectively. The brackets 22, 22' and the archwire 28 comprise a mandibular orthodontic system.

Figure 2:
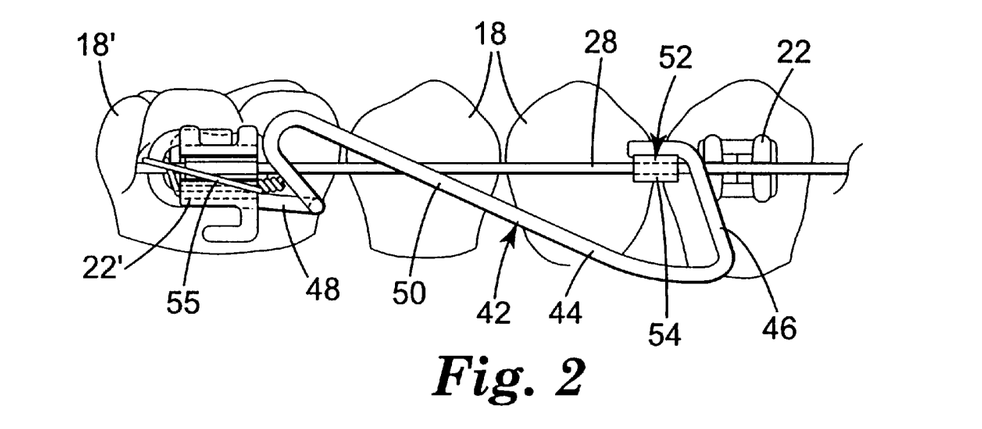
FIG. 2 is an enlarged side elevational view of an attachment device of the assembly shown in FIG. 1 along with representative mandibular teeth, mandibular brackets and a mandibular archwire connected to the brackets, wherein a molar bracket band and some of the brackets have been removed for purposes of illustration and wherein the view has been flattened (i.e., the curvature in directions along the length of the dental arch has been removed)

The assembly 10 also includes an interarch appliance 30 for repositioning the mandibular dental arch 14 relative to the maxillary dental arch 12. For purposes of illustration, the interarch appliance 30 depicted in FIGS. 1 and 2 is essentially the same as the appliances described in U.S. Pat. No. 5,651,672 which is incorporated by reference herein. However, any of the other non-removable intra-oral devices described above may also be used as alternatives, including the appliances with flexible members as described in U.S. Pat. Nos. 4,708,646, 5,352,116 and 5,435,721. The interarch appliance 30 may also be used with telescoping tube assemblies such as the appliances described in U.S. Pat. Nos. 3,798,773, 4,462,800, 4,551,095, 5,562,445 and 5,711,667, so long as the telescoping members do not detach from each other when the jaws are opened.

The interarch appliance 30 includes a lower end portion 32 having a coupler 34. The interarch appliance 30 also includes an upper end portion 36 having a coupler 38. In this instance the couplers 34, 38 comprise circular holes or openings, although other types of couplers may also be employed, including wire loops, crimpable connectors and the like.

The interarch appliance 30 also includes a middle portion 40 that is preferably covered by a plastic sheath. The portions 32, 36, 40 are preferably made of a unitary, resilient thin band of material, such as that described in the aforementioned U.S. Pat. No. 5,651,672. The interarch appliance has an inherent bias that tends to urge the middle portion 40 toward a normally straight orientation in order to provide a correction force for pushing one jaw relative to the other when the jaws are closed.

The assembly 10 includes an attachment device 42 for coupling the interarch appliance 30 to one of the orthodontic systems, such as the mandibular orthodontic system comprising the brackets 22, 22' and the archwire 28 as depicted in the drawings. The attachment device 42 includes a wire segment 44 having a mesial end section 46, a distal end section 48 and an intermediate section 50 located between the end sections 46, 48. An uppermost terminal end portion of the mesial end section 46 extends in a distal direction and is fixed to a crimpable connector 52 adapted to receive the mandibular archwire 28.

Figure 3:
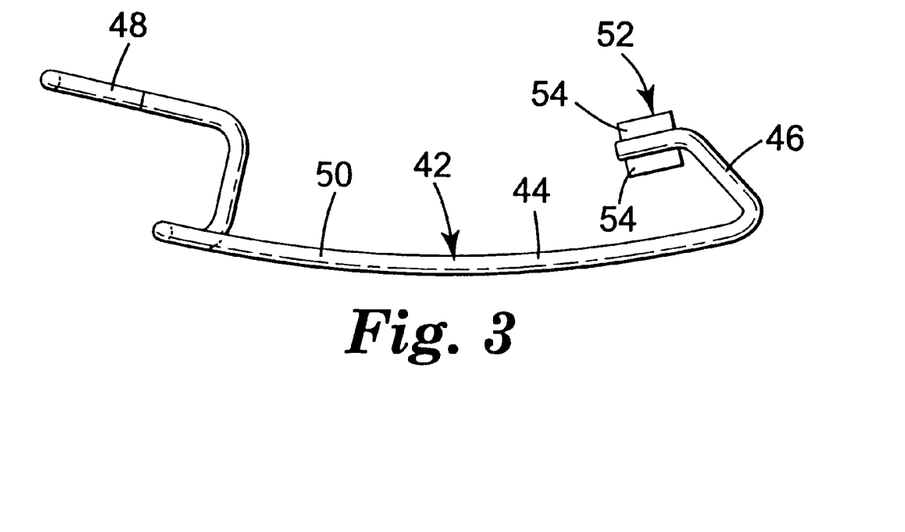
FIG. 3 is an enlarged plan view looking in a gingival direction of the attachment device alone shown in FIGS. 1 and 2, and depicting a crimpable connector and a distal end section of the device as they originally appear before installation.
Figure 4:
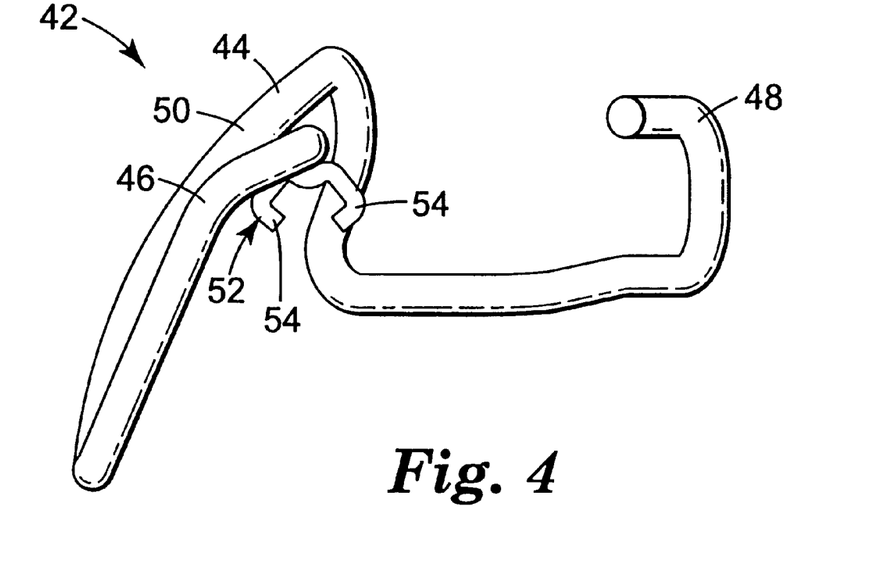
FIG. 4 is an end elevational view of the device shown in FIG. 3.

The crimpable connector 52 includes a pair of opposed, generally "C"-shaped wall portions 54 that extend around and partially define a passageway. The passageway has opposed open ends (i.e., open mesial and distal ends) and a side that is initially open as illustrated in FIGS. 3 and 4. The open side of the connector 52 extends along its bottom or gingival side in this embodiment although other constructions are also possible. The wall portions 54 are deformable in directions toward the passageway of the connector 52 for secure, non-rotatable connection to the mandibular archwire 28.

The mesial end section 46 extends from the connector 52 in a downwardly or gingival direction as well as preferably in a slight forwardly or mesial direction as depicted in FIGS. 3 and 4. The mesial end section 46 is also inclined outwardly in a buccolabial or facial direction. A lower end of the mesial end section 46 is connected to a lower end of the intermediate section 50. From the mesial end section 46, the intermediate section 50 is inclined in an upwardly (i.e., occlusal) and rearwardly (i.e., distal) direction, and crosses over a labial side of the mandibular archwire 28 as shown in FIGS. 1 and 2.

An upper end of the intermediate section 50 is integrally connected to an upper end of the distal end section 48. From the intermediate section 50, the distal end section 48 extends in a downwardly and mesially inclined direction, then in a lingual direction, and then in a distal direction. An outermost terminal end portion of the distal end section 48 extends upwardly and then mesially around the periphery of the buccal tube bracket 22'. Preferably, the distal end section 48 is received in grooves or recesses behind tiewings, flanges or other structure of the buccal tube bracket 22', and passes by a lingual side of the mandibular archwire 28 at a location distal to the buccal tube bracket 22'. Optionally, a wire ligature 55 extends around the distal end section 48 and around a portion of the buccal tube bracket 22' in order to securely fix the attachment device 42 to the buccal tube bracket 22'.

The lower coupler 34 of the interarch appliance 30 is connected to the wire segment 44. More particularly, the intermediate section 50 of the wire segment 44 extends through the opening of the lower coupler 34, and the lower end portion 32 is preferably slidable along the entire extent of the intermediate section 50. The extent of such sliding motion effectively spans the distance from the lower curve of the wire segment 44 where the mesial end section 46 connects to the intermediate section 50 to the upper curve of the wire segment 44 where the intermediate section 50 connects to the distal end section 48. As a consequence, the attachment device 42 of the present invention provides an enhanced range of sliding movement of the lower coupler 34 relative to the lower dental arch 14, the mandibular brackets 22 and the mandibular archwire 28 in comparison to previously known devices.

Preferably, the intermediate section 50 of the attachment device 40 is spaced sufficiently from the mandibular brackets 22, and in particular is spaced sufficiently from the mandibular brackets 22 that are mounted on the patient's lower bicuspid teeth, so that the interarch appliance 30 including the lower coupler 34 does not contact the mandibular brackets 22 or the mandibular archwire 28 as the patient's jaws are opened and closed. (To clarify the drawings, the lower bicuspid brackets 22 are not shown in FIG. 2.) Moreover, the inclination of the intermediate section 50 is selected to equal or at least approximate the direction of inclination of a hypothetical reference line extending between the upper coupler 38 and the lower end of the intermediate section 50, preferably during the entire range of movement of the jaws from a fully closed to a fully opened position, so that the lower coupler 34 encounters very little resistance to sliding movement along the intermediate section 50 as the jaws are opened or closed. As a result, both opening and closing movements of the upper and lower jaws are not unduly restricted.

Preferably, the crimpable connector 52 is spaced from adjacent brackets 22 when the patient's dental arches 12, 14 are fully closed, so that the restoring force presented by the interarch appliance 30 is not directed against the bracket 22 that is located mesially of the connector 52. Instead, the correcting force provided by the interarch appliance 30 is directed to the buccal tube bracket 22'. In use, the interarch appliance 30 urges the attachment device 42 in a mesial direction when the jaws are closed and the lower coupler 34 reaches the lower end of the intermediate section 50. Since the distal end section 48 is secured to the buccal tube bracket 22' and engages its distal side, the patient's lower jaw is urged forwardly as a result. Typically, the roots of the patient's molar teeth provide a stronger anchor for repositioning the patient's jaws than the roots of, for example, the patient's cuspid teeth, so that the entire lower jaw tends to move in a forwardly direction rather than just causing movement of the attached teeth relative to the jaw. Additionally, the provision of the band for securing the buccal tube bracket 22' to the patient's molar tooth helps ensure that the buccal tube bracket 22' will remain securely fixed to the patient's molar tooth.

The attachment device 42 of the present invention also reduces the amount of force or stress that is placed on other orthodontic elements, including the brackets 20, 22 and the archwires 24, 28. As a result, the present invention reduces the likelihood that the brackets 20, 22 will spontaneously debond from the underlying tooth surfaces during ordinary opening and closing movements of the patient's jaws, such as during eating or speech. Less stress is also imposed on the couplers 34, 38 of the interarch appliance 30, with the result that the likelihood of breakage of the appliance 30 in use is also reduced.

If desired, a stop such as a crimpable ball stop or crimpable collar may be installed in a location on a lower portion of the intermediate section 50, such as a location adjacent the mesial end section 46. The stop may be used at any point during the course of treatment to shorten the range of travel of the interarch appliance 30 along the intermediate section 50 in a downwardly direction. For example, if at some time during the course of treatment the orthodontist would like to increase the amount of force provided by the interarch appliance 30 on the patient's jaws when the jaws are closed, the stop can be installed between the coupler 34 and the lower end of the intermediate section 50 in order to ensure that the interarch appliance 30 will be bent to a smaller radius of curvature and thereby provide an increased amount of force when the patient's jaws are closed.

Preferably, the transverse cross-sectional area of the wire segment 44 is greater than the cross-sectional area of the lower archwire 28 in order to better withstand forces imposed by the interarch appliance 30 during movement of the patient's jaws. For example, the wire segment 44 may have a circular cross-sectional configuration with a diameter of 0.028 in. (0.7 mm). The wire segment 44 may be constructed of any suitable metallic material such as series 300 stainless steel. The wire segment 44 may be a drawn wire or a wire made by a casting, machining or metal injection molding process. The connector 52 may be fixed to the wire segment 44 by a welding, brazing or any other suitable process.

As another option, the wire segment 44 may have a non-circular cross-sectional configuration such as rectangular, square or the like, and the opening of the lower coupler 34 may have a mating configuration. The non-circular configurations of the wire segment 44 and the opening of the lower coupler 34 function to prevent pivotal movement of the interarch appliance 30 and the jaws are opened or closed, which may be preferred by some practitioners.

As shown in FIG. 1, a coupling pin 56 is provided to connect the interarch appliance 30 to one of the maxillary brackets 20, and in particular to the maxillary buccal tube bracket 20'. The coupling pin 56 includes an enlarged ball-shaped head 58 as well as a shank 60 that is fixed to the head 58. In the illustrated embodiment, the shank 60 is inserted into a passage of the maxillary buccal tube bracket 20', and an outer or mesial end of the shank 60 is bent in an angle to retain the pin 56 in coupled relation to the buccal tube bracket 20'.

Preferably, the outer end section of the pin shank 60 (i.e., the end section remote from the enlarged head 58) has a yield stress that is less than the yield stress of an intermediate section of the pin shank 60. Such construction enables the outer end section to be permanently deformed with less effort than the effort required to deform the intermediate section, and may be provided by annealing or partially annealing the outer end section. Further details and alternative coupling pins are described in pending U.S. patent application Ser. No. 09/197,309 filed Nov. 20, 1998 and entitled "ORTHODONTIC COUPLING PIN", the disclosure of which is expressly incorporated by reference herein.

Although not illustrated in the drawings, similar structure is presented on the opposite side of the patient's dental arches 12, 14. More particularly, a second interarch appliance similar to appliance 30 and a second attachment device similar to attachment device 42 are provided on the opposite side, so that a corrective force is presented to both sides of the lower arch in balanced relation as the patient's jaws are closed.

Figure 5:
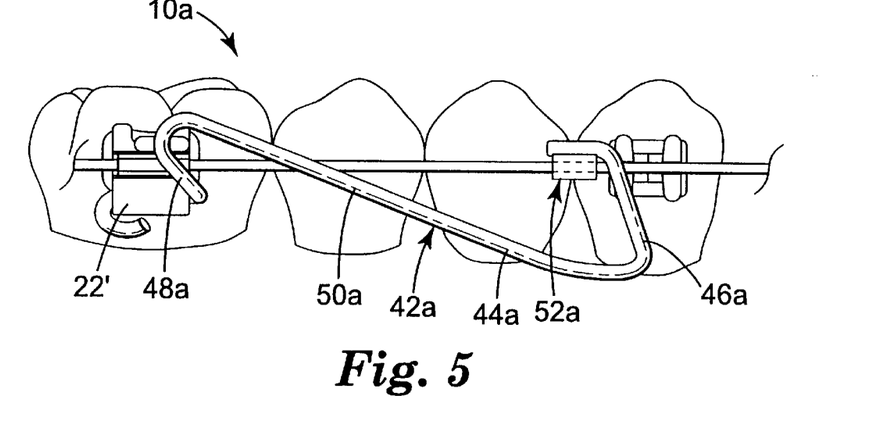
FIG. 5 is a view somewhat similar to FIG. 2 but in accordance with another embodiment of the invention.

An orthodontic assembly 10a with an attachment device 42a according to an alternative embodiment of the invention is illustrated in FIG. 5. The attachment device 42a includes a wire segment 44a having a mesial end section 46a and a connector 52a that are identical to the mesial end section 46 and connector 52 described above. The attachment device 42a also includes an intermediate section 50a that is somewhat similar to the intermediate section 50 but extends a somewhat greater distance in a distal direction than the intermediate section 50. In particular, the intermediate section 50a extends past a mesial side of the buccal tube bracket 22', where it connects with an upper portion of a distal end section 48a.

In this embodiment, the distal end section 48a extends downwardly and in a mesial direction from the intermediate section 50a, then in a lingual direction, and then in a distal direction through a passage of the buccal tube bracket 22'. An outer end portion of the distal end section 48a is bent by the practitioner in an arc as shown in FIG. 5 in order to secure the attachment device 42a to the buccal tube bracket 22'. Such construction eliminates the need for a ligature such as the ligature 55 described in connection with FIGS. 1 and 2. Optionally, the outer end portion of the distal end section 48a is annealed or partially annealed to provide a more compliant structure that can be easily bent by the practitioner, in a manner similar to annealing of the outer end portion of the pin shank 60 as described above.

Figure 6:
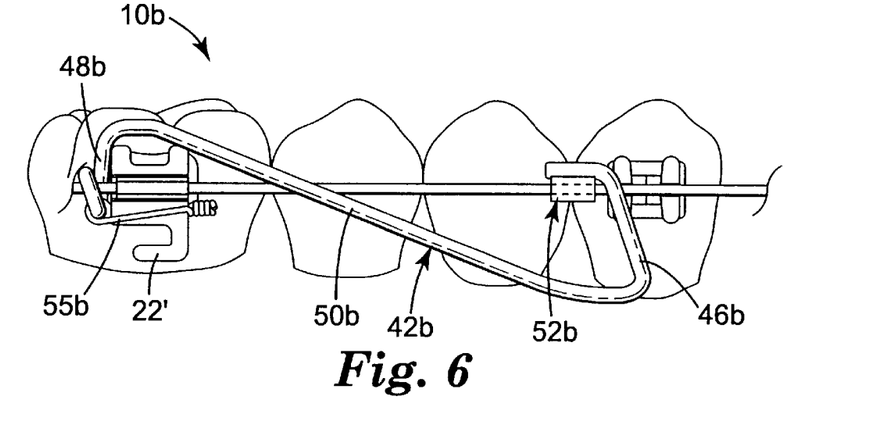
FIG. 6 is a view somewhat similar to FIG. 2 but showing yet another embodiment of the invention.

An orthodontic assembly 10b according to another embodiment of the invention is illustrated in FIG. 6, and includes an attachment device 42b having a mesial end section 46b and a connector 52b that are identical to the mesial end section 46 and connector 52 respectively described above. The attachment device 42b includes an intermediate section 50b that is somewhat similar to the intermediate section 50 but extends in this instance in a distal direction to the distal side of the buccal tube bracket 22'. The attachment device 42b has a distal end section 48b that is connected to an upper end of the intermediate section 50b, and from that point extends in a downwardly direction along a lingual side of the archwire 28, then in a buccolabial direction, then in an upwardly or occlusal direction and finally in a lingual direction. A wire ligature 55b extends through a passage in the buccal tube bracket 22' and around the distal end section 48b, and ends of the ligature 55b are twisted together in order to secure the distal end section 48b to the buccal tube bracket 22'.

Optionally, an outer end portion of the distal end section 48b is bent in an arc sufficient to completely encircle the archwire 28. The outer end portion of the distal end section 48b is optionally annealed or partially annealed as described above in connection with the distal end section 48a in order to facilitate bending.

Figure 7:
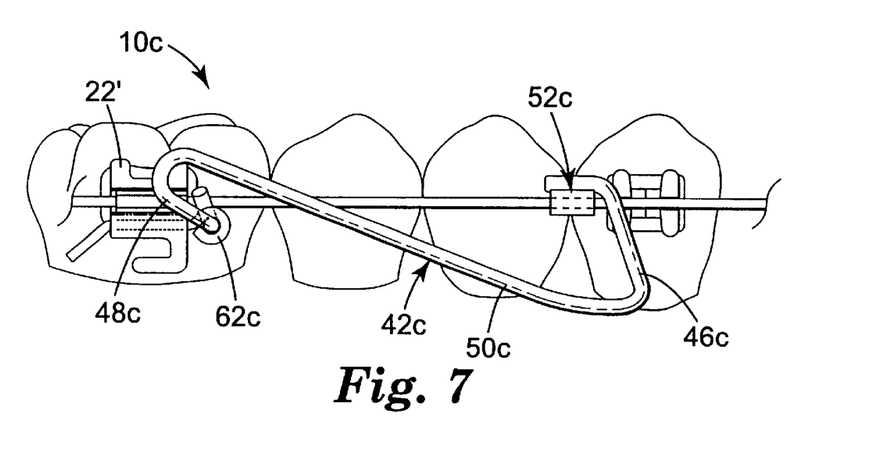
FIG. 7 is a view somewhat similar to FIG. 2 but illustrating still another embodiment of the invention.

Another embodiment of the invention is illustrated in FIG. 7, wherein an orthodontic assembly 10c includes an attachment device 42c having a mesial end section 46c and a connector 52c that are identical to the mesial end section 46 and connector 52 respectively described above. The attachment device 42c also includes an intermediate section 50c that is somewhat similar to the intermediate section 50a.

A distal end section 48c of the attachment device 42c extends in a downwardly and mesially inclined direction from the upper end of the intermediate section 50c, then in a lingual direction, and finally in an upwardly or occlusal direction. The lingually extending portion of the distal end section 48c passes through an aperture in a hook 62c. The hook 62c includes a shank that extends through a passage in the buccal tube bracket 22', and an outer, distal end of the hook 62c is bent as shown in FIG. 7 in order to secure the hook 62c as well as the attachment device 42c to the buccal tube bracket 22'.

Figure 8:
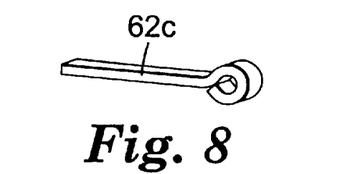
FIG. 8 is a perspective view of a hook alone of the attachment device shown in FIG. 7 as the hook appears before installation.

The hook 62c is shown alone in FIG. 8. Preferably, the shank of the hook 62c has a rectangular or square cross-sectional configuration that matches a rectangular or square cross-sectional shape of the passage in the buccal tube bracket 22'. As a consequence, the hook 62c is non-rotatable relative to the buccal tube bracket 22' in an arc about its longitudinal axis. Optionally, an outer end portion of the shank of the hook 62c is annealed or partially annealed in a manner similar to annealing of the coupling pin 56 as described above.

Figure 9:
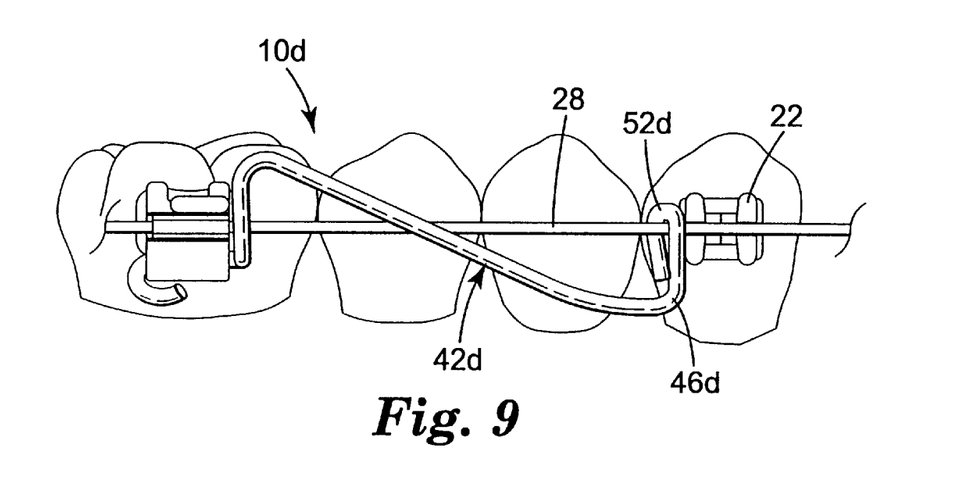
FIG. 9 is a view somewhat similar to FIG. 2 but showing a further embodiment of the invention.

FIG. 9 is an illustration of yet another embodiment of the invention, wherein an orthodontic assembly 10d includes an attachment device 42d that is the same as the attachment device 42a described above and shown in FIG. 5 except that the attachment device 42d includes a connector 52d that is somewhat different than the connector 52a. More particularly, the connector 52d is integrally connected to a mesial end section 46d of the attachment device 42d, and extends in a closed loop about the mandibular archwire 28. Preferably, the connector 52d initially has a shape of a partially open loop to enable the practitioner to readily install the attachment device 42d on the lower archwire 28 without removing the archwire 28 from the brackets 22. The loop is then squeezed together and closed by the practitioner using a pliers or other similar tool in order to secure the attachment device 42 to the lower archwire 28.

In practice, the attachment device 42d is made from a single wire segment that is shaped to the desired configuration. Remaining elements and aspects of the attachment device 42d are similar to the elements and aspects of the attachment device 42a described earlier and the reader is referred to that description for further details if desired.

Figure 10:
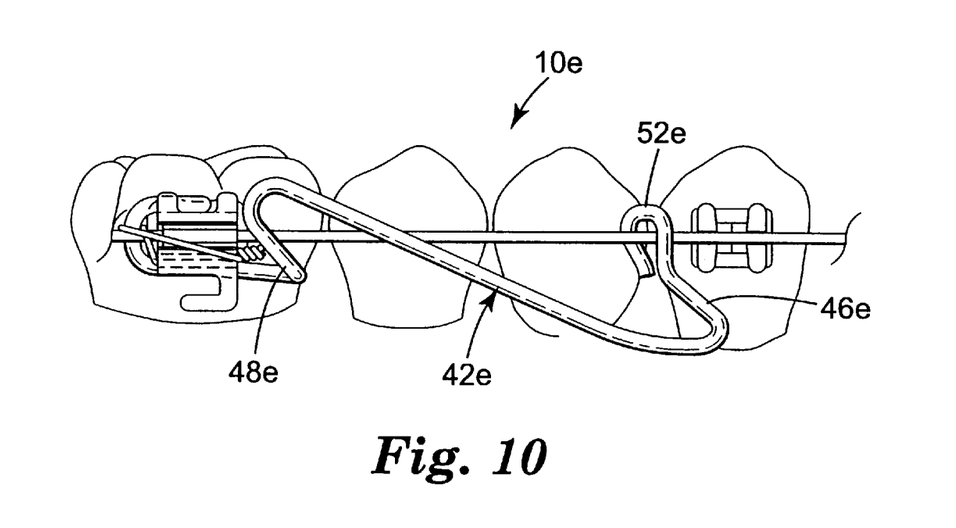
FIG. 10 is a view somewhat similar to FIG. 2 but showing an additional embodiment of the invention.

FIG. 10 shows a further embodiment of the invention, wherein an orthodontic assembly 10e includes an attachment device 42e that is essentially the same as the attachment device 42d, except that the attachment device 42e includes a mesial end section 46e that extends at an angle in a mesial and gingival direction from a connector 52e. Additionally, a distal end section 48e has a shape that is somewhat similar to the distal end section 48 illustrated in FIGS. 1 and 2.

Figure 11:
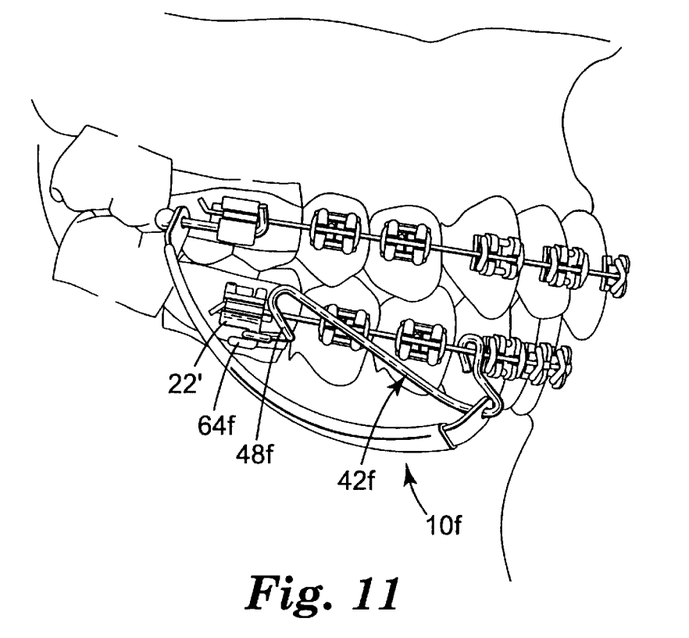
FIG. 11 is a view somewhat similar to FIG. 1 but showing another embodiment of the invention.

The embodiment of the invention that is illustrated in FIG. 11 concerns an orthodontic assembly 10f that includes an attachment device 42f that is essentially the same as the attachment device 42e described above. However, the attachment device 42f has a distal end section 48f that, in this instance, extends around a hook 64f of a buccal tube bracket 22'. Although not illustrated in the drawings, a ligature such as a wire ligature may be used to secure the distal end section 48f to the hook 64f.

Figure 12:
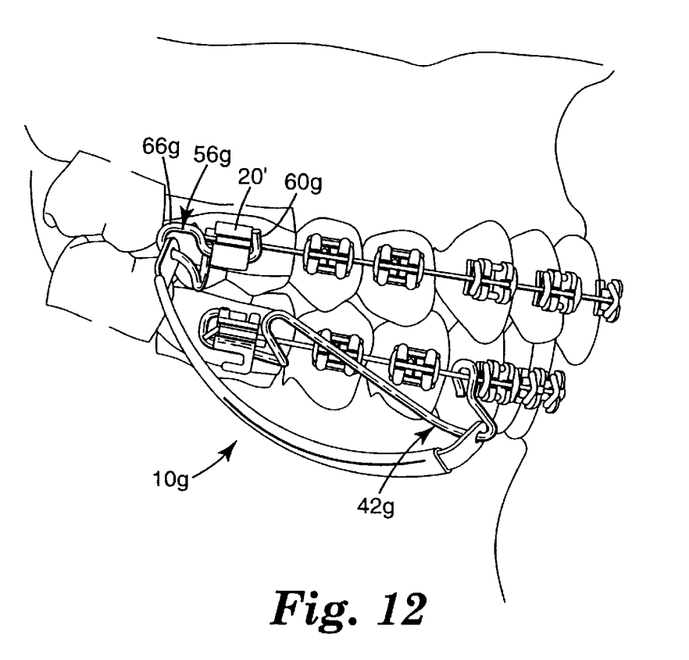
FIG. 12 is a view somewhat similar to FIG. 1 but showing yet an additional embodiment of the invention.

An orthodontic assembly 10g according to another embodiment of the invention is illustrated in FIG. 12 and includes an attachment device 42g that is the same as the attachment device 42e depicted in FIG. 10. However, the assembly 10g includes a coupling pin 56g that is somewhat different than the coupling pin 56 described above.

More particularly, the coupling pin 56g includes a shank 60g that is inserted into a passage of the maxillary buccal tube bracket 20', and an outer or mesial end of the shank 60g is bent at an angle to retain the pin 56g in coupled relation to the buccal tube bracket 20'. The pin 56g also includes a distal end segment 66g in the shape of a closed loop as shown in the drawings. From the buccal tube bracket 20', the distal end segment 66g first extends in a gingival direction, then in a distal direction, then in an incisal direction, then in a mesial direction, then curves toward an incisal direction, then in a lingual direction and finally in a gingival direction to form its loop-shaped configuration. Optionally, a braze or tack weld could be provided to help retain the loop in a closed configuration. Optionally, an outer end portion of the shank 60g is annealed or partially annealed in a manner similar to annealing of the coupling pin 56 as described above.

An orthodontic assembly 10h (FIG. 13) according to another embodiment of the invention includes an attachment device 42h that is identical to the attachment device 42e. The assembly 10h also includes a coupling pin 56h that is somewhat different than the coupling pin 56g.

Figure 13:
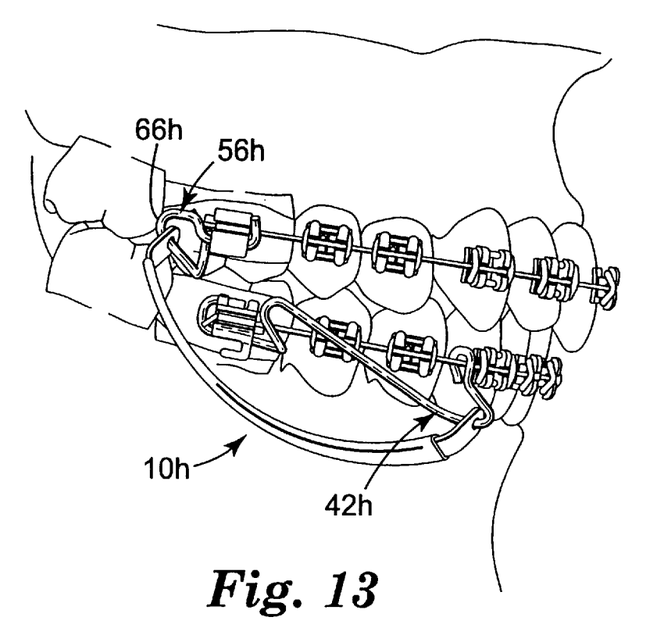
FIG. 13 is a view somewhat similar to FIG. 1 but illustrating yet another embodiment of the invention.

More particularly, the coupling pin 56h is essentially the same as the coupling pin 56g, except that a portion of a distal end segment 66h of the coupling pin 56h is inclined in a somewhat different direction. This inclined portion extends through the hole or upper coupler of the interarch appliance 30 as shown in FIG. 13 and is somewhat easier to fabricate in comparison to the construction shown in FIG. 12.

Figure 14:
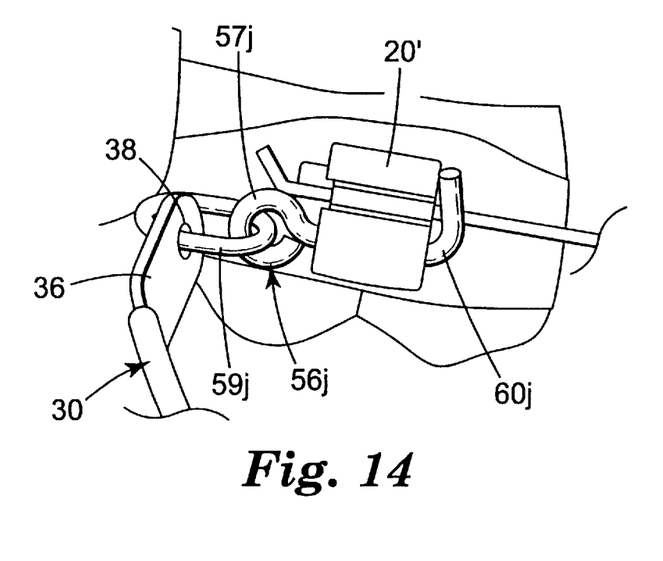
FIG. 14 is an enlarged fragmentary side elevational view of an alternative coupling pin of the invention for connecting an upper coupler of an interarch appliance to a maxillary buccal tube bracket.

Another alternative coupling pin 56j of the invention is illustrated in FIG. 14. The coupling pin 56j includes a shank 60j and a curved end portion or eyelet 57j that is integrally connected to the shank 60j. The coupling pin 56j also includes a loop 59j that passes through the eyelet 57j. The loop 59j is securely coupled to the eyelet 57j, but is movable relative to the eyelet 57j in a manner similar to movement of links of a chain.

The loop 59j passes through the coupler 38 of the upper end portion 36 of the interarch appliance 30. As one option, the loop 59j is installed in the coupler 38 as well as in the eyelet 57j by the manufacturer. Optionally, the loop 59j is made of a segment of wire that is formed into an oval, and ends of the wire segment are welded or brazed together to ensure that the loop 59j does not open during the course of treatment. As another option, the manufacturer may sell the loop 59j as partially open and initially detached from the eyelet 57j, and the practitioner may couple the loop 59j to the eyelet 57j after the shank 60j has been inserted into the buccal tube bracket 20'.

The loop 59j may be made of any one of a number of suitable metallic materials such as series 300 stainless steel. Preferably, the loop 59j, the eyelet 57j and the shank 60j are sufficiently rigid to resist elongation in use. Optionally, one or more additional loops may be provided and connected to the loop 59j in serial, chain-type fashion.

Preferably, the outer end section of the pin shank 60j (i.e., the end section remote from the eyelet 57j) has a yield stress that is less than the yield stress of an intermediate section of the pin shank 60j, similar to the construction of the outer end section of the pin shank 60 as described above. The shank 60j is initially straight. Once the shank 60j is placed into the passage of the buccal tube bracket 20', the outer end section of the pin shank 60j is bent in an arc as shown in FIG. 10 in order to retain the coupling pin 60j in secure, connected relation to the buccal tube bracket 20'.

The coupling pin 56j is an advantage, in that the combination of the loop 59j and the eyelet 57j enhance movement of the interarch appliance 30 in use. The mobility between the loop 59j and the eyelet 57j enables the appliance 30 to shift downwardly as the jaws are opened and to also pivot as needed. As a consequence, the patient can more readily spread the jaws apart to a fully open position and patient comfort is increased during such opening movement. The combination of the loop 59j and the eyelet 57j decreases the amount of torque stress placed on the upper end portion 36 of the appliance 30, thereby decreasing the likelihood of breakage of the appliance 30 or other elements during the course of treatment.

Optionally, a second coupling pin similar to coupling pin 56j may be provided for the lower end portion of the interarch appliance 30. In that instance, the shank of the second coupling pin is bent into a loop and connected to the attachment device (such as attachment device 42).

Figure 15:
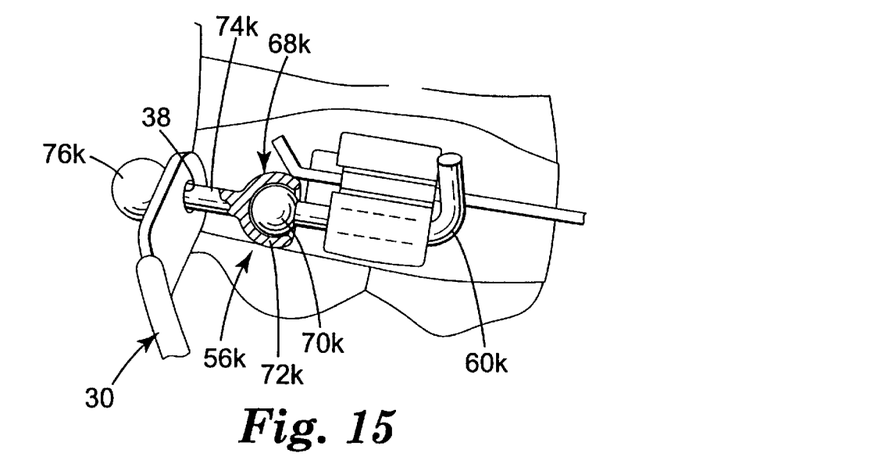
FIG. 15 is a view somewhat similar to FIG. 14 but showing another coupling pin of the invention, wherein part of the coupling pin is shown in section.

FIG. 15 is an illustration of a coupling pin 56k according to another embodiment of the invention. The coupling pin 56k includes a shank 60k as well as linkage 68k connected to the shank 60k. The linkage 68k is articulated.

In more detail, the linkage 68k includes a ball 70k that is integrally connected to the shank 60k, as well as a semi-spherical socket 72k that is movably connected to the ball 70k. The ball 70k is captured in the socket 72k, in a manner similar to a ball-and-socket joint. A rod 74k is integrally connected to the socket 72k and passes through the upper coupling 38 of the interarch appliance 30. An enlarged head 76k is integrally connected to the rod 74k to retain the coupling 38 on the rod 74k.

Figure 16:
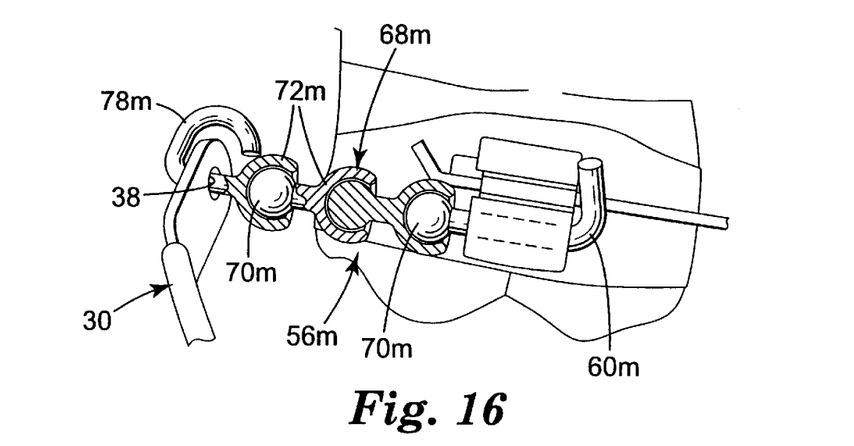
FIG. 16 is a view somewhat similar to FIG. 15 but illustrating yet another coupling pin of the invention.

A coupling pin 56m according to another embodiment of the invention is depicted in FIG. 16. The coupling pin 56m is somewhat similar to the coupling pin 56k, in that the coupling pin 56m includes a shank 60m as well as linkage 68m connected to the shank 60m. However, the linkage 68m includes three articulations, in contrast to the single articulation of the coupling pin 56k.

More specifically, the linkage 68m includes three balls 70m and three sockets 72m connected to respective balls 70m. The balls 70m and sockets 72m are similar in configuration to well-known ball chains that are often sold for jewelry, personal accessories and other items. The outermost socket 72m is connected to an eyelet 78m which passes through the upper coupling 38 of the interarch appliance 30.

Figure 17:
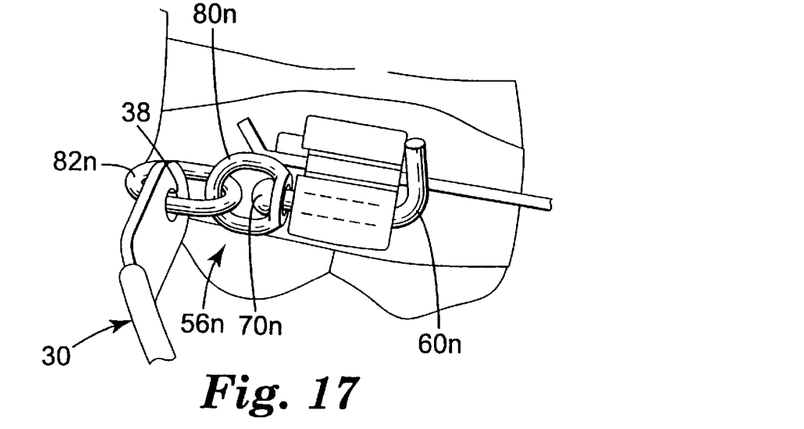
FIG. 17 is a view somewhat similar to FIG. 14 but depicting yet another coupling pin of the invention.

In FIG. 17, a coupling pin 56n according to another embodiment of the invention includes a shank 60n that is integrally connected to a ball head 70n. The shank 60n extends through an aperature in a flattened end of a first loop 80n. A second loop 82n passes through the first loop 80n and also passes through the upper coupling 38 of the interarch appliance 30.

The coupling pin and its various embodiments as described above may have other types of construction as well. For example, the linkage may comprise bead chain, box chain or any other type of suitable small chain similar to chains known in the art. The chain can include any type of flexible series of joined links. Such construction enhances movement of the interarch appliance 30 in use and increases patient comfort in the manner as described above in connection with the coupling pin 56j.

In FIGS. 2, 5–7 and 9–10, the brackets bonded to the patient's bicuspid teeth are not shown for purposes of more clearly illustrating the invention. However, the attachment device in its various embodiments of the invention functions well with the bicuspid brackets in place and in use, and in normal practice those brackets do not contact the connector of the interarch appliance (such as interarch appliance 30) as the latter slides along the intermediate section of the attachment device. The present invention is an advantage in that such bicuspid brackets can remain in place and facilitate corrective movements of the associated teeth as may be needed during the course of treatment, in contrast to prior art practices where such bicuspid brackets were often removed from the teeth to avoid interference with the interarch appliance while the latter was in use.

Those skilled in the art may recognize that a variety of modifications and additions to the presently preferred embodiments described above are possible without departing from the spirit of our invention. As one example, the interarch appliance 30 may be replaced by other interarch appliances, including some of the telescoping tube assemblies as described in the patents referenced above. Furthermore, the attachment device may be provided with other types of connectors for coupling to the archwire or to one or more brackets such as bicuspid brackets. Accordingly, the invention should not be deemed limited by the embodiments set out in detail above, but instead only by a fair scope of the claims that follow along with their equivalents.

What is claimed is:

1. An orthodontic assembly comprising:

an orthodontic system including a set of brackets and an archwire connected to each bracket;

an interarch appliance for repositioning the lower dental arch relative to the upper dental arch, the interarch appliance including a coupler; and an attachment device connected to the system, the attachment device including a wire segment, the coupler of the interarch appliance being connected to the wire segment for a sliding movement along the length of the wire segment, the wire segment crossing over the labial side of the archwire with sufficient space between the wire segment and the archwire such that the coupler of the interarch appliance is moveable along the wire segment past the archwire as the patient's jaws are opened.

2. An orthodontic assembly according to claim 1, wherein the interarch appliance includes an upper coupler, wherein a reference line extending from the upper coupler to the coupler connected to the wire segment extends at a certain angle relative to the archwire when the jaws are closed, and wherein the wire segment extends at an angle relative to the archwire that is approximately the same as that certain angle.

3. An orthodontic assembly according to claim 1, wherein the wire segment includes a mesial end section, and wherein a crimpable connector is fixed to the mesial end section for connection to the archwire.

4. An orthodontic assembly according to claim 1, wherein the wire segment includes a distal end section that extends around at least a portion of one of the brackets.

5. An orthodontic assembly according to claim 4, wherein the bracket that the wire segment extends at least partially around is a buccal tube bracket.

6. An orthodontic assembly according to claim 5 and including a hook having an opening for receiving the distal end section of the wire segment and for coupling the distal end section to the buccal tube bracket.

7. An orthodontic assembly according to claim 5 and including a ligature for ligating the distal end section of the wire segment to the buccal tube bracket.

8. An orthodontic assembly according to claim 1, wherein the wire segment includes an intermediate section that is substantially straight and wherein the coupler remains in contact with the intermediate section as the patient's jaws are moved from a fully closed position to a fully opened position.

9. An orthodontic assembly according to claim 1, wherein the coupler includes an opening for receiving the wire segment.

10. An orthodontic assembly according to claim 1, wherein the set of brackets includes a buccal tube bracket, and wherein the buccal tube bracket substantially limits movements of the wire segment as the patient's jaws are closed.

11. An orthodontic assembly according to claim 1, wherein the interarch appliance is an elongated, resilient force module having an inherent bias toward a normally straight orientation.

12. An orthodontic assembly according to claim 1 and including a coupling pin having a shank, an eyelet connected to the shank and a loop passing through the eyelet, wherein the loop is connected to the interarch appliance.

13. An orthodontic assembly according to claim 1, wherein the wire segment includes an intermediate section and a distal end section, wherein the distal end section is connected to a buccal tube bracket of the set of brackets, and wherein the distal end section and the intermediate section each extend upwardly to a common location that is located distally of a mesial side of the buccal tube bracket.

14. An orthodontic assembly comprising:
a maxillary orthodontic system including a set of maxillary brackets and a maxillary archwire connected to each maxillary bracket;
a mandibular orthodontic system including a set of mandibular brackets and a mandibular archwire connected to each mandibular bracket;
an interarch appliance for repositioning the mandibular dental arch relative to the maxillary dental arch, the interarch appliance including an upper end portion connected to the maxillary system, the interarch appliance also including a lower end portion having a coupler; and
an attachment device connected to the mandibular system, the attachment device including a wire segment, the coupler of the interarch appliance being connected to the wire segment for sliding movement along the length of the wire segment, the wire segment crossing over the labial side of the mandibular archwire with sufficient space between the wire segment and the mandibular archwire such that the coupler of the interarch appliance is movable along the wire segment past the mandibular archwire as the patient's jaws are opened.

15. An orthodontic assembly according claim 14, wherein the uppermost end portion includes a coupler, wherein a reference line extending from the coupler of the upper end portion to the coupler of the lower end portion extends at a certain angle relative to the mandibular archwire when the jaws are closed, and wherein the wire segment extends at an angle relative to the mandibular archwire that is approximately the same as that certain angle.

16. An orthodontic assembly according to claim 14, wherein the wire segment includes a mesial end section with a crimpable connector for connection to the mandibular archwire.

17. An orthodontic assembly according to claim 14, wherein the wire segment includes a distal end section that extends around at least a portion of one of the mandibular brackets.

18. An orthodontic assembly according to claim 17 and including a hook having an opening for receiving the distal end section of the wire segment and for coupling the distal end section to the bracket around which the wire segment at least partially extends.

19. An orthodontic assembly according to claim 17 and including a ligature for ligating the distal end section to the mandibular bracket around which the wire segment at least partially extends.

20. An orthodontic assembly according to claim 14, wherein the wire segment includes an intermediate section that is substantially straight and wherein the coupler remains in contact with the intermediate section as the patient's jaws are moved from a fully closed position to a fully opened position.

21. An orthodontic assembly according to claim 14, wherein the coupler includes an opening for receiving the wire segment.

22. An orthodontic assembly according to claim 14, wherein the interarch appliance is an elongated, resilient force module having an inherent bias toward a normally straight orientation.

23. An orthodontic assembly according to claim 14, wherein the wire segment includes an intermediate section and a distal end section, wherein the distal end section is connected to a buccal tube bracket of the set of mandibular brackets, and wherein the distal end section and the intermediate section each extend upwardly to a common location that is located distally of a mesial side of the buccal tube bracket.

24. An orthodontic assembly according to claim 14 and including a coupling pin for connecting the upper end portion of the interarch appliance to one of the maxillary brackets, wherein the coupling pin includes a shank, an eyelet integrally connected to the shank and a loop connected to the upper end portion, and wherein the loop passes through the eyelet.

25. An orthodontic assembly comprising an interarch appliance for repositioning the lower arch relative to the upper arch and a coupling pin, wherein the interarch appliance includes an end portion with a coupling, wherein the coupling pin includes a shank and linkage connected to the shank and the coupling, and wherein the linkage is articulated relative to the shaft and relative to the coupling.

26. An orthodontic assembly according to claim 25 wherein the linkage includes an eyelet integrally connected to the shank and a loop for connection to the interarch, wherein the loop passes through the eyelet.

27. An orthodontic assembly according to claim 25 wherein the linkage includes a chain segment.

28. An orthodontic assembly according to claim 25 wherein the linkage includes at least one closed loop.

29. An orthodontic assembly according to claim 25 wherein the shank includes an intermediate section and an outer end section, and wherein the outer end section has a yield stress that is less than the yield stress of the intermediate section.

30. An orthodontic assembly according to claim 25, wherein the end portion of the interarch appliance is an upper end portion for connection to the maxillary arch.

31. An orthodontic assembly according to claim 25, wherein the interarch appliance is an elongated, resilient force module having an inherent bias toward a normally straight orientation.

32. An orthodontic coupling pin comprising a shank and linkage connected to the shank, wherein the linkage is articulated, wherein the linkage includes a chain segment, and wherein the chain segment comprises a ball chain.

* * * * *